United States Patent [19]

Slaugh

[11] Patent Number: 5,243,120
[45] Date of Patent: Sep. 7, 1993

[54] PROCESS FOR THE PRODUCTION OF OLEFINS

[75] Inventor: Lynn H. Slaugh, Houston, Tex.

[73] Assignee: Shell Oil Company, Houston, Tex.

[21] Appl. No.: 880,116

[22] Filed: May 7, 1992

Related U.S. Application Data

[63] Continuation-in-part of Ser. No. 785,581, Oct. 30, 1991, abandoned.

[51] Int. Cl.$^5$ .............................................. C07C 6/02
[52] U.S. Cl. ................................... 585/646; 585/647; 585/664
[58] Field of Search ............... 585/646, 643, 647, 670, 585/671

[56] References Cited

U.S. PATENT DOCUMENTS

| | | | |
|---|---|---|---|
| 3,261,879 | 7/1966 | Banks | 260/683 |
| 3,340,322 | 7/1967 | Heckelsberg | 260/683 |
| 3,621,073 | 9/1968 | McGrath et al. | |
| 3,637,892 | 1/1972 | McGrath et al. | 260/683 D |
| 3,658,927 | 4/1972 | Crain et al. | 260/666 A |
| 3,668,270 | 6/1972 | Martin et al. | 260/683 D |
| 3,760,026 | 9/1973 | Reusser et al. | 260/683 D |
| 3,786,112 | 1/1974 | Reusser et al. | 260/683 D |
| 3,792,108 | 2/1974 | Arganbright | 260/683 D |
| 3,872,180 | 3/1975 | Nakatomi | 260/683 D |
| 3,915,897 | 10/1975 | Reusser et al. | 502/210 |
| 4,180,524 | 12/1979 | Reusser et al. | 585/644 |
| 4,895,997 | 1/1990 | Hamilton et al. | 585/329 |
| 4,940,827 | 7/1990 | Janssen et al. | 585/646 |
| 4,962,267 | 10/1990 | Slaugh | 585/670 |
| 4,996,386 | 2/1991 | Hamilton et al. | 585/646 |
| 5,043,520 | 8/1991 | Hamilton | 585/646 |
| 5,057,644 | 10/1991 | Lin et al. | 585/850 |
| 5,120,894 | 6/1992 | McCauley | 585/664 |
| 5,120,896 | 6/1992 | Kemp et al. | 585/646 |

FOREIGN PATENT DOCUMENTS

| | | |
|---|---|---|
| 1034968 | 7/1978 | Canada . |
| 1128091 | 3/1966 | United Kingdom . |
| 1205677 | 2/1968 | United Kingdom . |
| 1471151 | 5/1974 | United Kingdom . |

Primary Examiner—Anthony McFarlane
Attorney, Agent, or Firm—Pamela J. McCollough

[57] ABSTRACT

This invention relates to a process for treating olefinic hydrocarbon mixtures with a catalyst system comprising an admixture of a disproportionation catalyst comprising an element selected from the group consisting of molybdenum, tungsten, rhenium and mixtures thereof, and optionally cobalt, and an isomerization catalyst prepared by impregnating a porous alumina support with a metal compound decomposable to an oxide upon calcination wherein said metal is selected from the group consisting of potassium, rubidium, cesium and mixtures thereof and subsequently calcining the resulting material at a temperature of from about 450° C. to about 750° C., thus producing increased yields of detergent range, i.e., $C_{10}$–$C_{16}$, olefins.

20 Claims, No Drawings

PROCESS FOR THE PRODUCTION OF OLEFINS

This is a continuation-in-part of co-pending application Ser. No. 785,581, filed Oct. 30, 1991, now abandoned.

FIELD OF THE INVENTION

This invention relates to a process for increasing the production of detergent range olefins by subjecting olefinic hydrocarbons having higher and lower molecular weights to a catalyst system comprising an admixture of a disproportionation catalyst and a double bond isomerization catalyst.

BACKGROUND OF THE INVENTION

Reactions of olefinic molecules in the presence of metal-containing catalysts to produce other olefinic molecules are known in the art as "disproportionation" reactions. A typical olefin disproportionation process is illustrated by U.S. Pat. No. 3,261,879, issued Jul. 19, 1966, to Banks, wherein two similar non-symmetrical molecules of an olefin react in the presence of certain catalysts to produce one olefin of a higher carbon number and one olefin of a lower carbon number such as, for example, propylene disproportionation by the process of U.S. Pat. No. 3,261,879 to produce ethylene and butylenes.

As used in this application, disproportionation process means the conversion of olefinic hydrocarbons into similar olefinic hydrocarbons of higher and lower numbers of carbon atoms per molecule. Where the reactant comprises mixtures of olefins having the double bond located internally or in the alpha position, a mixture of product is obtained comprising olefins having both a larger and a smaller number of carbon atoms than the feed olefin. Such an operation is useful in many instances. For example, a more plentiful hydrocarbon can be converted to a less plentiful and therefore more valuable hydrocarbon. One instance of such a conversion and the one to which this invention is directed occurs when the process of this invention is used to convert both higher and lower molecular weight olefins to olefins in the $C_{10}$–$C_{16}$ range, a range of olefins especially suitable for the manufacture of detergents. Another instance of a disproportionation reaction having considerable value is the disproportionation of propylene to produce ethylene and butene.

A variety of catalysts have been employed for conducting disproportionation reactions, such as those disclosed in U.S. Pat. No. 3,340,322, issued Sep. 5, 1967; U.S. Pat. No. 3,637,892, issued Jan. 25, 1972; U.S. Pat. No. 3,760,026, issued Sep. 18, 1973; U.S. Pat. No. 3,792,108, issued Feb. 12, 1974; U.S. Pat. No. 3,872,180, issued Mar. 18, 1975; and British Patent Specification No. 1,128,091, published Mar. 16, 1966.

It is also known that the presence of a catalyst which possesses double bond isomerization activity in a disproportionation process is advantageous because it increases the rate of conversion and makes possible the production of a wider range of symmetrical olefins such as butene-2. In addition, the isomerization activity permits the exhaustive cleavage of high molecular weight monoolefins with ethylene to lower molecular weight monoolefins such as propylene and isobutene. British Patent No. 1,205,677, published Sep. 16, 1970, provides a catalyst which comprises an olefin disproportionation component and a Group VIII noble metal double bond isomerization component, i.e., palladium, platinum or ruthenium. Another catalyst system which accomplishes the same results is obtained by physically mixing catalytic magnesium oxide with tungsten oxide on silica catalyst. Other catalysts which have been developed include those obtained by copromoting an olefin disproportionation catalyst such as tungsten oxide on silica with minor amounts of the oxides of niobium, tantalum or vanadium to provide the double bond isomerization activity.

U.S. Pat. No. 3,786,112 discloses a catalyst comprising a physical mixture of an olefin disproportionation catalyst and a double bond isomerization catalyst wherein the double bond isomerization catalyst has been treated with an alkali metal or alkaline earth metal compound.

U.S. Pat. No. 5,043,520 discloses a catalyst comprising a physical mixture of an olefin disproportionation catalyst and a double bond isomerization catalyst wherein the double bond isomerization catalyst comprises an acidic zeolite.

U.S. Pat. No. 4,996,386 discloses a single catalyst composition for concurrent double bond isomerization and disproportionation which contains ferrierite, cobalt and molybdenum and/or tungsten incorporated into an alumina hydrogel.

U.S. Pat. No. 4,180,524 discloses a single catalyst composition containing a support, uranium and at least one of molybdenum, tungsten or rhenium, which provides double bond isomerization activity as well as olefin disproportionation activity.

SUMMARY OF THE INVENTION

The present invention relates to a process for treating olefinic hydrocarbons with a catalyst system comprising an admixture of a disproportionation catalyst comprising an element selected from the group consisting of molybdenum, tungsten, rhenium and mixtures thereof, and optionally cobalt, and an isomerization catalyst prepared by impregnating a porous alumina support with a metal compound decomposable to an oxide upon calcination wherein said metal is selected from the group consisting of potassium, rubidium, cesium and mixtures thereof and subsequently calcining the resulting material at a temperature of from about 450° C. to about 750° C., thus producing increased yields of detergent range, i.e., $C_{10}$–$C_{16}$, olefins.

It has been found that when using the same volumes of catalyst in each process, the catalyst system of the present process results in enhanced yields of $C_{10}$–$C_{16}$ and in particular, $C_{11}$–$C_{14}$ olefins when compared to a process utilizing a disproportionation catalyst and an isomerization catalyst in a conventional two-bed configuration. The catalyst system in the present invention can be in a stacked bed or layered configuration containing at least four stacks or, it can comprise a physical mixture of the disproportionation and isomerization catalysts. The stacked bed or layered configuration can be accomplished by arranging the disproportionation catalyst and the isomerization catalyst in layers, preferably beginning with the isomerization catalyst and ending with the disproportionation catalyst. The physical mixture catalyst of this invention can be prepared by combining a catalyst comprising an element selected from the group consisting of molybdenum, tungsten, rhenium and mixtures thereof, and optionally cobalt, on an inorganic oxide support with a catalyst prepared by impregnating a porous alumina support with a metal compound decomposable to an oxide upon calcination wherein said metal is selected from the group consisting of potassium, rubidium, cesium and mixtures thereof and subsequently calcining the resulting material at a temperature of from about 450° C. to about 750° C.

DESCRIPTION OF THE PREFERRED EMBODIMENTS

In the process of the instant invention, the treatment of an olefinic hydrocarbon to produce enhanced yields of $C_{10}$–$C_{16}$ olefins is accomplished by contacting the olefinic hydrocarbon with a catalyst system comprising an admixture of a disproportionation catalyst comprising an element selected from the group consisting of molybdenum, tungsten, rhenium and mixtures thereof, and optionally cobalt, and an isomerization catalyst prepared by impregnating a porous alumina support with a metal compound decomposable to an oxide upon calcination wherein said metal is selected from the group consisting of potassium, rubidium, cesium and mixtures thereof and subsequently calcining the resulting material at a temperature of from about 450° C. to about 750° C.

Olefinic hydrocarbons which are subjected to treatment in the process of this invention include $C_3^+$ olefinic hydrocarbons, or $C_3^+$ internal olefins in combination with ethylene. A useful group of feed materials are olefinic hydrocarbons having carbon numbers ranging from $C_2$ to about $C_{100}$, preferably from $C_2$ to about $C_{60}$, and more preferably linear, olefinic hydrocarbons having carbon numbers ranging from about $C_4$ to about $C_{40}$. Examples of compounds most suitable for disproportionation according to this invention are acyclic 1- and 2-alkenes, and alkyl and aryl derivatives thereof having from 3 to 20 carbon atoms per molecule. Some specific examples of such olefins are propylene, 1-butene, 2-butene, 1-pentene, 2-pentene, 1-hexene, 2-heptene, 1-octene, 2-nonene, 1-dodecene, 2-tetradecene, 1-hexadecene, 2-methyl-1-butene, 2-methyl-2-butene, 3-methyl-1-butene, 1-phenylbutene-2, and 3-heptene.

The feed should be essentially free of impurities which adversely affect the reaction. A subsequent reactivation of the catalyst to remove the effect of such impurities can be made repeatedly by heat treatment with air, followed by the use of an inert gas such as, for example, argon, helium or nitrogen.

The catalyst system of this invention is prepared by admixing a supported disproportionation catalyst containing an element selected from the group consisting of molybdenum, tungsten, rhenium and mixtures thereof, and optionally cobalt, and a double bond isomerization catalyst prepared by impregnating a porous alumina support with a metal compound decomposable to an oxide upon calcination wherein said metal is selected from the group consisting of potassium, rubidium, cesium and mixtures thereof, and subsequently calcining the resulting material at a temperature of from about 450° C. to about 750° C. The catalyst comprising the catalyst system in the present invention can be admixed in several ways. For example, the catalysts can be arranged in a stacked bed or layered configuration containing at least four stacks, preferably more than four stacks, or alternatively, the catalyst system can comprise a physical mixture of the disproportionation and isomerization catalysts. In a preferred embodiment, the catalysts are arranged in a stacked bed configuration.

The disproportionation catalyst component of the catalyst system comprises molybdenum and/or tungsten and/or rhenium supported on an alumina-containing support. In a preferred embodiment, the catalyst also contains cobalt. Any conventional catalytic grade of alumina including the beta or gamma forms can be used. The catalyst can contain other materials which do not substantially promote undesirable side reactions. For example, an alumina support or base can contain silica, magnesia, titania or other bases in amounts which do not change the essential characteristics of the reaction.

The disproportionation catalyst component can be prepared by any conventional method such as dry mixing, coprecipitation or impregnation. For example, a 10–100 mesh alumina can be impregnated with an aqueous solution containing molybdenum salts, such as ammonium dimolybdate and optionally, cobalt salts, such as cobalt nitrate.

In a preferred embodiment, the disproportionation catalyst component in the instant invention is a cobalt/molybdenum catalyst prepared by impregnating alumina with an impregnation solution combining an aqueous cobalt solution and an aqueous molybdenum solution. The cobalt solution consists of cobalt salts dissolved in water. A wide range of cobalt compounds are suitable, such as cobalt nitrate, cobalt hydroxide, cobalt acetate, cobalt oxalate, or cobalt oxide, with cobalt nitrate being preferred. The molybdenum solution consists of a water-soluble source of molybdenum oxide such as ammonium heptamolybdate or ammonium dimolybdate dissolved in water. Hydrogen peroxide may also be used to aid in solution preparation in some cases. A preferred method for preparing the molybdenum solution consists of adding hydrogen peroxide to the solution in the range of about 0.1 to about 1.0 mole of hydrogen peroxide per mole of molybdenum. Optionally, a suitable soluble amine compound such as monoethanolamine, propanolamine or ethylenediamine may be added to the molybdenum solution in order to aid in stabilization of the solution.

Following impregnation, the resulting material is dried and calcined. Drying is accomplished by conventional means. It may be carried out by forced draft drying, vacuum drying, air drying or similar means. Drying temperatures are not critical and depend upon the particular means utilized for drying. Drying temperatures will typically range from about 50° C. to about 150° C.

After drying, the material is calcined to produce the finished catalyst. The material may be calcined in an oxidizing or neutral atmosphere, although air is preferred. However, if binders and/or lubricants are used the material is heated in an oxygen-containing atmosphere, preferably air, in order to burn out the binders and lubricants. Calcining temperatures will typically range from about 300° C. to about 600° C. Burn-out temperatures will depend on the concentration of oxygen in the burn-out atmosphere as well as the burn-out time involved. Typically, burn-out temperatures will range from about 300° C. to about 600° C. Drying, calcining and burn-out may be combined in one or two steps. Most frequently, the calcining and/or burn-out steps are combined using an oxygen-containing atmosphere. Following these steps, it is desirable to activate the catalysts by subjecting them to a flow of nitrogen at elevated temperature, i.e., a temperature in the range of from about 500° C. to about 700° C.

The disproportionation catalyst component typically contains from about 5 percent by weight to about 18 percent by weight molybdenum, about 8 percent by weight to about 32 percent by weight tungsten or from about 1 percent by weight to about 20 percent by weight rhenium. When mixtures of molybdenum, and tungsten and rhenium are utilized, the catalyst typically contains from about 5 percent by weight to about 32 percent by weight molybdenum and/or tungsten and/or rhenium. When the catalyst contains cobalt, the final catalyst contains from about 0.1 percent by weight to about 5 percent by weight cobalt. These types of catalysts are well known in the art and can be prepared according to the prior art, such as but not limited to aforementioned U.S. Pat. No. 3,261,879 and U.S. Pat. No. 3,365,513 (both of which are incorporated by reference herein) for more specific details about these types of catalysts.

The double bond isomerization catalyst component in the catalyst system of the instant invention is prepared for example, by impregnating or otherwise providing a porous alumina support with an alkali metal compound decomposable upon calcination to the oxide where the metal is selected from the group consisting of potassium, rubidium, cesium and mixtures thereof and then calcining the resultant composition at a temperature ranging from about 450° C. to about 750° C., preferably from about 500° C. to about 700° C. Calcining below the desired lower temperature limits results in catalysts which are not active, and calcining above the desired upper temperature limits results in excessive sintering with a resultant degradation of catalyst properties. It is thought that the decomposable compound(s) during the calcination react after intermediate oxide formation with the alumina to form a metal aluminate. Suitable impregnating alkali metal compounds that decompose during calcination include, for example, carbonates, bicarbonates, hydroxides, chelates, alkoxylates and salts of other weak acids or salts of strong acids that decompose upon calcination such as the nitrates.

The calcination is carried out in any atmosphere: vacuum, reducing, neutral or oxidizing, with reducing and oxidizing atmospheres being preferred. When the decomposable compound has an organic anionic moiety such as carboxylate, alkoxylate, chelate, etc., it is preferred to carry out the calcination in a reducing atmosphere such as nitrogen or an oxidizing atmosphere such as air or oxygen. Calcination times are not activated by flowing nitrogen, hydrogen or other inert gases over the catalyst at elevated temperatures, i.e., from about 500° C. to about 700° C., preferably about 575° C., for about sixteen hours.

The alkali metals used to form the isomerization catalyst component in the present invention are potassium, rubidium and cesium. Combinations of these metal can also be utilized. Preferred impregnating materials for the alumina are potassium carbonates, potassium carboxylates and potassium nitrate. Salts of strong acids that do not completely decompose such as, for instance, sulfates and halides are not satisfactory.

The alumina employed in the isomerization catalyst component can be any of the variety of available aluminas or alumina hydrates, such as alumina gel, activated alumina, gamma alumina and the like. The most suitable aluminas for use in the present invention are found to be those having surface areas ranging from about 1 m²/g to about 500 m²/g, preferably from about 50 m²/g to about 400 m²/g. In a preferred embodiment, the alumina support is gamma alumina. Aluminas are readily available commercially which are suitable for use in the instant invention. The following table lists several commercial gamma aluminas and their properties which are suitable.

| Alumina | Surface Area, m²/g | Pore Vol. Cc/gm | Na, ppm | SO₄⁼ % wt. | Fe₂O₃ % wt. | Cl⁻ % wt. |
|---|---|---|---|---|---|---|
| CCI (a) | 252 | 0.8 | 160 | 0.06 | — | 0.02 |
| KA-201 (b) | 365 | 0.42 | 600 | 0.03 | — | 0.01 |
| RA-1 (c) | 263 | 0.26 | 4700 | 0.02 | 0.18 | — |
| ACCP (d) | 225 | 0.68 | 580 | 0.6 | — | 0.6 |
| Norton | 218 | 0.62 | 0.51 | 0.03 | — | 0.03 |
| CATAPAL (e) | 348 | 0.91 | — | — | — | — |
| FILTROL (f) | 214 | 0.82 | — | — | — | — |

(a) Catalysts & Chemicals, Inc., now United Catalysts
(b) Kaiser
(c) Reynolds Corp.
(d) American Cyanamid Corp.
(e) Conoco Corp.
(f) Filtrol Corp.

Any conventional methods known for adding the metal oxide or decomposable compound to the alumina can be employed. A preferred method is to soak the alumina support pellets in an aqueous solution of the decomposable metal compounds(s), dry the impregnated alumina, and then calcine at temperatures in the range of from about 450° C. to about 750° C., preferably from about 500° C. to about 700° C. Dry mixing can also be used. Since the metal oxide or decomposable compound is primarily reacting with the surface alumina, both external and internal pore surface, then the maximum amount of impregnating compound that can be effectively utilized will depend on the surface area. Ordinarily, the molar ratio of metal added to alumina will range from about 2:1 to about 1:50, preferably from about 1:1 to about 1:25. Preferably, the weight of the metal oxide or decomposable compound added will range from about 0.1 percent by weight to about 30 percent by weight, more preferably from about 1 percent by weight to about 25 percent by weight, and most preferably, from about 5 percent by weight to about 20 percent by weight measured as the metal. In a preferred embodiment, a given portion of alumina pellets is impregnated with just enough aqueous solution of decomposable metal to fill the pore volume of the alumina, then dried at temperatures of up to about 125° C., and then calcined at temperatures in the range of from about 450° C. to about 750° C., preferably from about 500° C. to about 700° C.

In one embodiment of the present process, the disproportionation catalyst and isomerization catalyst components of the catalyst system are arranged in a stacked bed or layered configuration. Typically, the number of stacks or layers is at least four, preferably more than four.

In another embodiment, the catalyst system of the instant invention is prepared by mixing the disproportionation catalyst and the double bond isomerization catalyst, thus forming a physical mixture of the two catalysts. When preparing a physical mixture of the two catalysts, it is desirable to have the catalysts in a form which is compatible one with the other in order to facilitate mixing. The catalysts may be, for example, in the form of powders, extrudates, pills and the like prior to mixing the two catalysts together. The amounts of disproportionation catalyst and double bond isomerization catalyst used in a physical mixture can vary within wide ranges. Preferably the ratio of disproportionation catalyst to double bond isomerization catalyst in the physical mixture is from about 0.1:1 to about 10:1, and preferably from about 1:3 to about 3:1. Particularly preferred is a 1:1 ratio of disproportionation catalyst to double bond isomerization catalyst in the physical mixture.

The catalyst system must be activated prior to use in the instant process. Although each of the individual catalysts can be activated prior to admixing the two catalysts, it is preferred that the catalyst system be activated after the disproportionation catalyst and isomerization catalyst have been admixed and placed in a suitable reactor. While activation is usually accomplished by contacting the catalyst system under vacuum or with an inert gas at elevated temperatures, other activation methods such as contact with various gases such as hydrogen at elevated temperatures, can be used. The temperature, contact times, and other conditions of activation have been reported in the prior art and are generally the same conditions which are utilized to activate a disproportionation catalyst. Typically, the activation conditions include a temperature in the range of from about 300° C. to about 900° C. for about 30 minutes to about 24 hours.

The process for treating the olefinic hydrocarbons of the invention can be carried out either batchwise or continuously, using a fixed catalyst bed, or a stirrer equipped reactor or other mobile catalyst contacting process as well as any other well known contacting technique. Preferred reaction conditions, e.g., temperature, pressure, flow rates, etc., vary somewhat depending upon the specific catalyst composition, the particular feed olefin, desired products, etc. The process is carried out at temperatures ranging from about 10° C. to about 350° C. and at pressures in the range of about 15 psig to about 500 psig. The reaction is usually effected in a liquid phase and if desired, liquid reaction diluents are utilized. Examples of suitable diluents are hydrocarbons free from aliphatic unsaturation, such as acyclic or alicyclic alkanes of from 6 to 12 carbon atoms, i.e. hexane, isooctane and cyclohexane. Also exemplary would be monoaromatic compounds such as benzene and toluene. If the diluent is added, it is present in amounts up to 20 moles of diluent per mole of olefinic reactants.

The operable range of contact time for the process of this invention depends primarily upon the operating temperature and the activity of the catalyst system, which is influenced by surface area, promoter concentration, activation temperature, etc. In general, the distribution of products is not drastically altered by variation in contact time. Shorter contact times are usually associated with higher temperatures, but, when larger amounts of higher molecular weight products are desired, a suitable combination of contact time and temperature is selected. With proper selection of conditions and contact times, very high efficiency of conversion to desired products can be obtained.

In this application, space rates are given in WHSV (weight hourly space velocity; weight of reactant feed per weight of catalyst per hour).

With a fixed bed reactor, continuous flow operation at pressures in the range of about 15 psig to about 500 psig, preferably about 50 psig to about 250 psig, with catalyst systems having densities ranging from about 0.5 gram per cc to about 1.0 gram per cc and surface areas greater than about 50 m²/g, and at temperatures in the range of about 10° C. to about 350° C., preferably about 100° C. to about 250° C., weight hourly space velocities in the range of about 0.1 to about 10.0 parts by weight of olefinic hydrocarbon feed per part by weight of catalyst per hour are suitable. The space velocity is adjusted according to changes in density of feed due to change of pressure or temperature, and variation in reaction temperature and the activity of the catalyst. The higher space velocities in general are associated with higher reaction temperatures.

The catalyst system of the present invention is advantageous with respect to a catalyst system in which the disproportionation and isomerization catalysts are not admixed in that a different mixture of product olefins is obtained. The catalyst system in the present invention results in maximized yields of the desired detergent range olefins, i.e., $C_{10}$–$C_{16}$ olefins. The ability to shift the mixture of product olefins to the desired detergent range olefin product is particularly useful in maximizing the economic return from any given olefin feedstock.

The ranges and limitations provided in the instant specification and claims are those which are believed to particularly point out and distinctly claim the instant invention. It is, however, understood that other ranges and limitations that perform substantially the same function in substantially the same manner to obtain the same result are intended to be within the scope of the instant invention as defined by the instant specification and claims.

The process of the instant invention will be further described below by the following examples which are illustrative and which are not to be construed as limiting the invention.

ILLUSTRATIVE EMBODIMENTS

Catalyst Preparation

Catalyst System 1

Catalyst System 1 is a catalyst system comprising a cobalt/molybdenum disproportionation catalyst component and a potassium carbonate on alumina double bond isomerization catalyst component in a stacked bed or layered configuration. The system comprises ten stacks or layers, five of each of the catalyst components.

The disproportionation catalyst component was prepared using a conventional dry pore volume impregnation technique. A solution suitable for impregnating 100 grams of calcined alumina support with a pore volume of 0.79 cm³/g was prepared as follows. An impregnation solution was made by heating 14.8 grams of water to 120° C. and adding thereto 5.10 grams of cobalt carbonate, 16.57 grams of ammonium dimolybdate, 33.9 grams of ammonium hydroxide and enough 24% aqueous ammonia to bring the solution to a total volume of 79 milliliters. After adding the entire solution to the alumina support in several small portions with intermediate agitations, the impregnated support was dried overnight at 150° C. and calcined in air for 2 hours at 450° C.

The double bond isomerization catalyst component was prepared by dissolving 15 Grams of anhydrous $K_2CO_3$ in 45 milliliters of deionized water. This solution was poured on 85 grams of Kaiser grade A-210 alumina (14–30 mesh) while the latter is being stirred. The volume of the solution and the weight of the alumina was proportioned to essentially fill the pores in the alumina without excess solution remaining after impregnation. The impregnated material was dried at 100° C. for 18 hours in air. The dried material was then calcined in a tube of flowing nitrogen for 16 hours at 575° C. The nitrogen flow rate was 2.7 liters/gram of catalyst/hour. Analysis indicated that the composition contained about 9.3 percent by weight of potassium measured as the potassium metal.

Similar catalysts can be prepared, for example by using solutions of potassium nitrate, potassium bicarbonate, potassium acetate and potassium nitrate.

Comparative Catalyst System A

Comparative Catalyst System A is a conventional catalyst system in which the isomerization catalyst and the disproportionation catalyst are separated in the reactor and are not admixed.

The disproportionation catalyst component was prepared using a conventional dry pore volume impregnation technique. A solution suitable for impregnating 100 grams of calcined alumina support with a pore volume of 0.79 cm$^3$/g was prepared as follows. An impregnation solution was made by heating 14.8 grams of water to 120° C. and adding thereto 5.10 grams of cobalt carbonate, 16.57 grams of ammonium dimolybdate, 33.9 grams of ammonium hydroxide and enough 24% aqueous ammonia to bring the solution to a total volume of 79 milliliters. After adding the entire solution to the alumina support in several small portions with intermediate agitations, the impregnated support was dried overnight at 150° C. and calcined in air for 2 hours at 450° C.

The double bond isomerization catalyst component was prepared by dissolving 15 Grams of anhydrous $K_2CO_3$ in 45 milliliters of deionized water. This solution was poured on 85 grams of Kaiser grade A-210 alumina (14–30 mesh) while the latter is being stirred. The volume of the solution and the weight of the alumina was proportioned to essentially fill the pores in the alumina without excess solution remaining after impregnation. The impregnated material was dried at 100° C. for 18 hours in air. The dried material was then calcined in a tube of flowing nitrogen for 16 hours at 575° C. Analysis indicated that the composition contained about 93 percent by weight of potassium measured as the potassium metal.

Catalyst Testing

Example 1

Catalyst System 1 was tested utilizing the following procedure. Ten grams of the isomerization catalyst component and ten grams of the disproportionation catalyst component were layered or stacked in alternating two gram stacks, i.e., five stacks of each catalyst component, beginning with the isomerization catalyst component, i.e., a two gram layer of the isomerization catalyst component followed by a two gram layer of the disproportionation catalyst component, in a stainless steel reactor. The catalyst was heated at a temperature of 575° C. under flowing nitrogen for 12 hours to remove any residual water from the catalyst. The catalyst was then cooled to 250° F. and feed was introduced upflow at a weight hourly space velocity (WHSV) of 1.0. The feed for these reactions is a double bond equilibrium mixture of $C_4$–$C_{40}$ linear olefins prepared by the oligomerization of ethylene and subsequent isomerization of the product. The feed contains approximately 1.5% branched olefins.

The product collected, as determined by a gas chromatography analysis, containing 26.1 percent by weight of $C_{10}$–$C_{16}$ olefins.

Comparative Example A

Comparative Catalyst System A was tested utilizing the following procedure. Ten grams of the isomerization catalyst component and ten grams of the disproportionation catalyst component were separately placed in a stainless steel reactor. The isomerization catalyst component was placed in the bottom of the reactor and the disproportionation catalyst component was placed at the top of the reactor. The two catalyst components were separated in the reactor by glass wool. The reactors were heated at a temperature of 575° C. under flowing nitrogen for 12 hours to remove an residual water from the catalyst. The reactors then cooled to 250° F. and feed was introduced upflow at a weight hourly space velocity (WHSV) of 1.0. The feed for these reactions is a double bond equilibrium mixture of $C_4$–$C_{40}$ linear olefins prepared by the oligomerization of ethylene and subsequent isomerization of the product. The feed contains approximately 1.5% branched olefins.

The product collected, as determined by a gas chromatography analysis, containing 24.1 percent by weight of $C_{10}$–$C_{16}$ olefins.

Discussion of Results

As can be seen from the above results, the catalyst system prepared according to the invention (Catalyst System 1) results in 26.1 percent by weight of $C_{10}$–$C_{16}$ olefins, whereas the conventional system in which two separate catalyst beds are used (Comparative Catalyst System A) results in 24.1 percent by weight of $C_{10}$–$C_{16}$ olefins. This represents an 8.3 percent by weight increase in the yields of $C_{10}$–$C_{16}$ olefins when using the catalyst system of the present invention.

What is claimed is:

1. A process for producing improved yields of $C_{10}$–$C_{16}$ olefins from olefinic hydrocarbon mixtures having carbon numbers ranging from $C_2$ to about $C_{100}$, which process comprises contacting said olefinic hydrocarbons with a catalyst system consisting essentially of an admixture of a disproportionation catalyst consisting essentially of a heavy metal selected from the group consisting of molybdenum, tungsten, rhenium and mixtures thereof, deposited on an inorganic oxide support and a double bond isomerization catalyst prepared by impregnating a porous alumina support with a metal compound decomposable to an oxide upon calcination wherein said metal is selected from the group consisting of potassium, rubidium, cesium and mixtures thereof, and subsequently calcining the resulting material at a temperature of from about 450° C. to about 750°.

2. The process of claim 1 wherein said disproportionation catalyst additionally consists of cobalt.

3. The process of claim 1 wherein said disproportionation catalyst consists of from about 8 percent by weight to about 32 percent by weight heavy metal.

4. The process of claim 3 wherein said disproportionation catalyst consists of from about 8 percent by weight to about 18 percent by weight molybdenum.

5. The process of claim 2 wherein said disproportionation catalyst consists of from about 1 percent by weight to about 5 percent by weight cobalt and from 8 percent by weight to about 32 percent by weight heavy metal.

6. The process of claim 5 wherein said disproportionation catalyst consists of from about 2.5 percent by weight to about 4 percent by weight cobalt and from about 8 percent by weight to about 18 percent by weight molybdenum.

7. The process of claim 1 wherein following calcination, the double bond isomerization catalyst is activated by heating the calcined material in the presence of nitrogen at a temperature in the range of from about 500° C. to about 700° C.

8. The process of claim 1 wherein said double bond isomerization catalyst is calcined at a temperature ranging from about 500° C. to about 700° C.

9. The process of claim 8 wherein said double bond isomerization catalyst is calcined in an inert atmosphere.

10. The process of claim 8 wherein said double bond isomerization catalyst is calcined in a reducing atmosphere.

11. The process of claim 1 wherein the metal compound added to the alumina support in said double bond isomerization catalyst ranges from about 0.1 to about 30 percent by weight measured as the metal.

12. The process of claim 11 wherein the metal compound added to the alumina support in said double bond isomerization catalyst ranges from about 1 to about 25 percent by weight measured as the metal.

13. The process of claim 12 wherein the metal compound added to the alumina support in said double bond isomerization catalyst ranges from about 5 to about 20 percent by weight measured as the metal.

14. The process of claim 1 wherein the metal compound added to the alumina support in said double bond isomerization catalyst is selected from the group consisting of potassium carbonates, potassium carboxylates, potassium nitrate and mixtures thereof.

15. The process of claim 14 wherein the metal compound added to the alumina support in said double bond isomerization catalyst is potassium carbonate.

16. The process of claim 1 wherein said olefinic hydrocarbons have carbon numbers ranging from $C_2$ to about $C_{60}$.

17. The process of claim 1 wherein said process is carried out at a temperature in the range of from about 10° C. to about 350° C. and a pressure in the range of from about 15 psig to about 500 psig.

18. The process of claim 1 wherein said catalyst system consists of alternating layers of said disproportionation catalyst and said double bond isomerization catalyst in a stacked bed configuration wherein said system consists of at least four stacks.

19. The process of claim 1 wherein said catalyst system consists of a physical mixture of said disproportionation catalyst and a said double bond isomerization catalyst.

20. The process of claim 19 wherein said catalyst system consists essentially of a ratio of disproportionation catalyst to double bond isomerization catalyst in the range of from about 0.1:1 to about 10:1 is used.

* * * * *